| United States Patent [19] | [11] Patent Number: 4,742,049 |
| Baker et al. | [45] Date of Patent: May 3, 1988 |

[54] SEMISYNTHETIC ERYTHROMYCIN ANTIBIOTICS

[75] Inventors: William R. Baker, Vernon Hills; Jerry D. Clark, Waukegan, both of Ill.

[73] Assignee: Abbott Laboratories, Chicago, Ill.

[21] Appl. No.: 870,489

[22] Filed: Jun. 4, 1986

[51] Int. Cl.[4] ...................... A61K 31/70; C07H 17/08
[52] U.S. Cl. ........................................ 514/29; 536/7.4
[58] Field of Search ..................... 514/29; 536/7.4, 7.2

[56] References Cited

FOREIGN PATENT DOCUMENTS 59086 5/1977 Japan .

OTHER PUBLICATIONS

*Chemical Abstracts* 89:44035g, abstracting an article from the *Polish Journal of Chemistry*, 52(2), 315–319, (1978).

*Chemical Abstracts* 90:152554e, abstracting a Japanese patent publication 78,144,589, dated 12/15/78, based on application 77/59,086, dated 5/21/77.

*Primary Examiner*—Nicky Chan
*Attorney, Agent, or Firm*—Martin L. Katz; Michael J. Roth

[57] ABSTRACT

Semisynthetic antibiotics with improved therapeutic properties made from erythromycin are disclosed. 11,12-Cyclic carbamates of erythromycin, its derivatives, and their salts and esters show superior in vitro antimicrobial activity and reduced hepatotoxicity compared to the parent compounds.

5 Claims, No Drawings

SEMISYNTHETIC ERYTHROMYCIN ANTIBIOTICS

TECHNICAL FIELD

This invention relates to antibiotics for use in the chemotherapy of antimicrobial infections, and more particularly to antibiotics made from erythromycin which exhibit high antimicrobial activity and improved therapeutic ratios.

BACKGROUND ART

Erythromycin and common derivatives are widely used and exhibit desirable activity against a number of gram-positive pathogens. Since some pathogens are less susceptible than others to these drugs, high doses of these antibiotics are occasionally necessary in the treatment of serious or widespread infections. As with all drugs, toxic effects are sometimes observed at higher dosage levels, particularly in patients who are seriously compromised by infection and thus are most in need of treatment. Unfortunately, improvements in potency and spectrum are often accompanied by an increase in toxicity, so that later generation drugs usually represent a compromise between these competing considerations. As a result, there is a continuing search for antibiotics which are more potent against certain organisms, or, preferably, against all organisms, than those currently used. Desirably, such drugs will have an improved therapeutic ratio, which is the ratio of the effective therapeutic or prophylactic dose to the toxic dose, usually expressed in terms of the $ED_{50}/LD_{50}$ ratio.

It is an object of this invention to provide novel compounds which are derivatives of erythromycin, and which have greater in vitro and in vivo potency against certain organisms than erythromycin, and increased therapeutic ratios in comparison to erythromycin.

This and other objects of this invention will be more fully understood by reference to the following disclosure.

DISCLOSURE OF THE INVENTION

This invention provides novel erythromycin A 11,12-cyclic carbamate compounds and pharmaceutically acceptable salts and esters thereof. In structural terms, this invention provides compounds of the formula

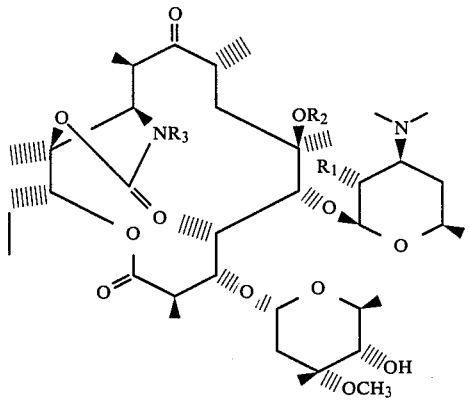

where $R_1$ is hydroxyl or O-acyl of 2 to 20 carbon atoms, $R_2$ is hydrogen or methyl and $R_3$ is hydrogen, hydroxy, alkyl, alkoxy, heteroalkyl, aryl, heteroaryl, dimethylaminoalkyl, acyl, or sulfonyl, and pharmaceutically acceptable salts thereof. Especially preferred is 6-O-methyl erythromycin A 11,12-[N-2-(dimethylamino)ethyl]cyclic carbamate, i.e., a compound according to the foregoing formula in which $R_2$ is methyl, $R_1$ is hydroxyl, and $R_3$ is 2-dimethylaminoethyl.

The term alkyl is used herein to mean straight and branched chain radicals, including, but not limited to methyl, ethyl, n-propyl, isopropyl, n-butyl, sec-butyl, isobutyl, tert-butyl, and the like.

The term alkoxy is used herein to mean straight and branched chain oxygen ether radicals, including, but not limited to methoxy, ethoxy, isopropoxy, n-butoxy, sec-butoxy, isobutoxy, tert-butoxy, and the like.

The term acyl is used herein to mean straight or branched chain carbonyl radicals, including but not limited to, formyl, acetyl, propionyl, butyryl, isobutyryl and the like.

The term aryl is used herein to mean substituted and unsubstituted aromatic radicals, including, but not limited to phenyl, 1-naphthyl, 2-naphthyl and the like.

Surprisingly, the compounds of this invention also offer improved in vitro and in vivo antibiotic potency against certain organisms in comparison to erythromycin. Further, these compounds provide an improved therapeutic ratio in comparison to potent erythromycin derivatives of the prior art. Especially notable is the reduced hepatotoxicity observed for these compounds in comparison with erythromycin A in standard rat hepatocyte models.

At least one compound of this invention (the preferred N-dimethylaminoethyl carbamate) has been determined via testing in sensitive animal models to cause much less gastointestinal motility and associated side-effects than the parent erythromycin compound. Increased gastrointestinal motility is often seen in macrolide antibiotics of the prior art and with other compounds of this invention. While it is apparently a pharmacologic effect of the drugs rather than a toxic effect, this side effect makes such prior art compounds less preferred because the increased motility can manifest itself as cramping, nausea and/or vomiting.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

INDUSTRIAL APPLICABILITY

The compounds of the present invention can be used in the form of salts derived from inorganic or organic acids. Among the more common salts and esters of macrolide antibiotics are the acetate, estolate (lauryl sulfate salt of the propionate ester), ethyl succinate, gluceptate (glucoheptonate), lactobionate, stearate, and hydrochloride forms. Other acid salts used in the pharmaceutical arts are the following: adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, gluconate, glycerophosphate, hemisulfate, heptonate, hexanoate, hydrobromide, hydroiodide, 2-hydroxy-ethanesulfonate, lactate, maleate, methanesulfonate, 2-naphthalenesulfonate, nicotinate, oxalate, pamoate, pantothenate, pectinate, persulfate, 3-phenylpropionate, picrate, pivalate, propionate, succinate, tartrate, thiocyanate, tosylate, and undecanoate. Although quaternized macrolide compounds are, in general, drastically less active than the parent compound in-vivo, basic nitrogen-containing groups can be quaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

This invention also provides methods of treating and preventing infection by susceptible organisms in a human or lower animal host in need of such treatment, which method comprises administration to the human or lower animal host a therapeutically effective amount of a compound or composition of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques.

Total daily dose of the compounds of this invention administered to a host in single or divided doses may be in amounts, for example, from 0.01 to 50 mg/kg body weight daily and more usually 0.1 to 15 mg/kg body weight daily. Dosage unit compositions may contain such amounts or submultiples thereof to make up the daily dose. It will be understood, however, that the specific therapeutically effective dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's injection, U.S.P. and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectibles.

Suppositories for rectal administration can be prepared by mixing the drug with a suitable nonirritating excipient such as cocoa butter or a polyethylene glycol which is solid at ordinary temperatures but liquid at the rectal temperature and will therefore melt in the rectum and release the drug.

Solid dosage forms for oral administration may include capsules, tablets, pills, powders, prills and granules. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric and other release-controlling coatings.

Liquid dosage forms for oral administration may include pharmaceutically acceptable emulsions, microemulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well known in the medical arts. In general, treatment regimens according to the present invention comprise administration to a patient in need of such treatment from about 100 milligrams to about 5,000 milligrams (preferably 500 to 2,000 milligrams) of the compound of this invention per day in multiple doses or, preferably, in a single dose of from about 250 milligrams to about 1,000 milligrams.

In general, the compounds of this invention are synthesized via an intramolecular Michael reaction. The 6-O-methyl erythromycin A 11,12-carbamates ($R_1$=OH, $R_2$=$CH_3$) are prepared from 6-O-methyl erythromycin A (1) in the manner indicated in schemes 1 and 2 below, while erythromycin A carbamates ($R_1$=OH, $R_2$=H) are prepared from the corresponding erythromycin A 11,12-cyclic carbonate (10) in the manner indicated in scheme 3 below. Thus, 6-O-methyl erythromycin A compounds are reacted with acetic anhydride and triethylamine ($Ac_2O$/TEA) to form the 2'-acetate, and the cladinose sugar is protected by acylation with benzylchloroformate and 4-dimethylaminopyridine (DMAP) at −20° C. The resulting compound is an 11,12-diol which is converted to the carbonate and then to an acyl imidazole (6) using excess sodium hexamethyldisilazide [$NaN(TMS)_2$, also called sodium bis-trimethylsilyl amide] at a temperature of −35° C. and excess carbonyldiimidazole (CDI) at room temperature (RT). Ammoniolysis of the product producues the 12-O-carbamate (7) which is reacted with potassium t-butoxide in tetrahydrofuran (THF) between −5° C. and 5° C. to yield the cyclic carbamate. If a substituted amine is used instead of ammonia, the potassium t-butoxide can be omitted and the corresponding N-substituted carbamates (8) are obtained by reaction in dimethylformamide (DMF) at RT. Where the amine is a liquid, the solvent may be omitted entirely. The protecting groups are removed by methanolysis at the 2'-position, followed by reduction with $H_2$/Pd/C, and the desired compounds (9) are obtained.

Erythromycin A 11,12-cyclic carbonates (10) are acylated at the 2' position in the manner previously described, heated at reflux with tetramethylguanidine and then reacted with benzylchloroformate and DMAP to afford the unsaturated ketone (11). This intermediate is converted to the acyl imidazole (12) with excess $NaN(TMS)_2$ and CDI, and the remainder of the synthesis proceeds as with the 6-O-methyl compounds.

Scheme 1

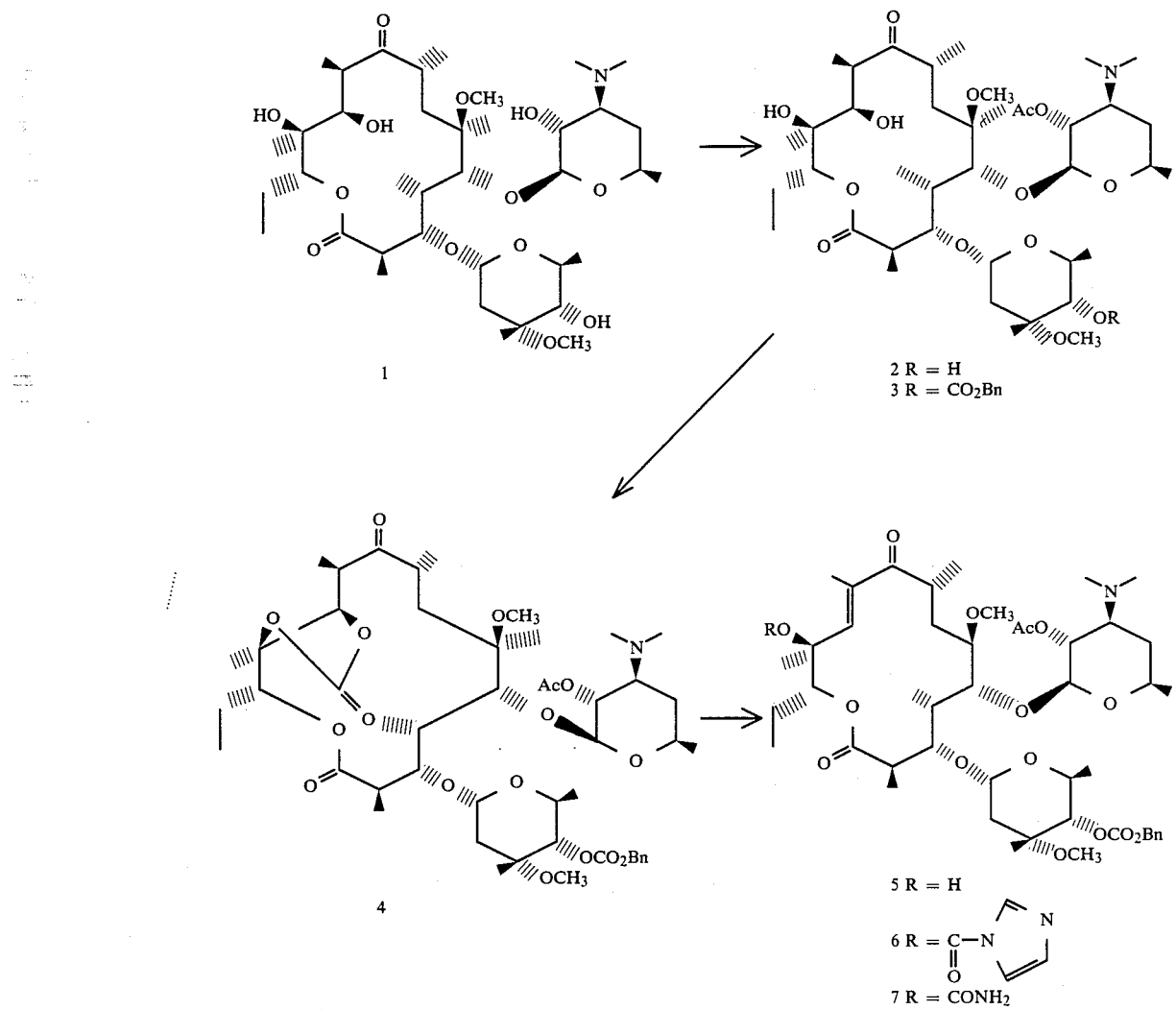

Scheme 2
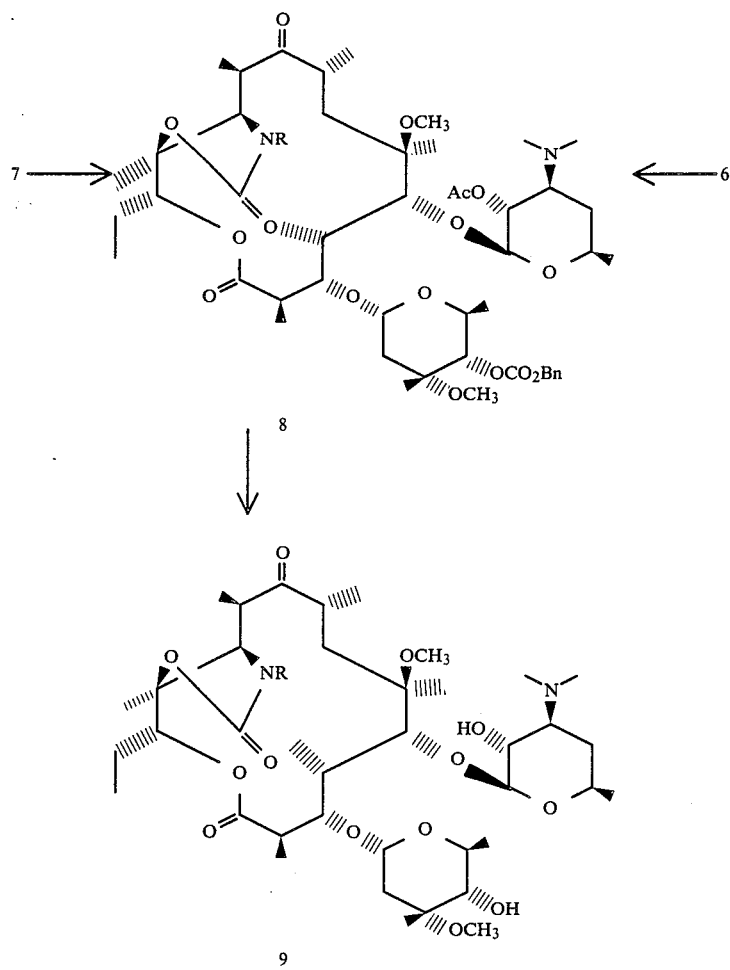
Scheme 3
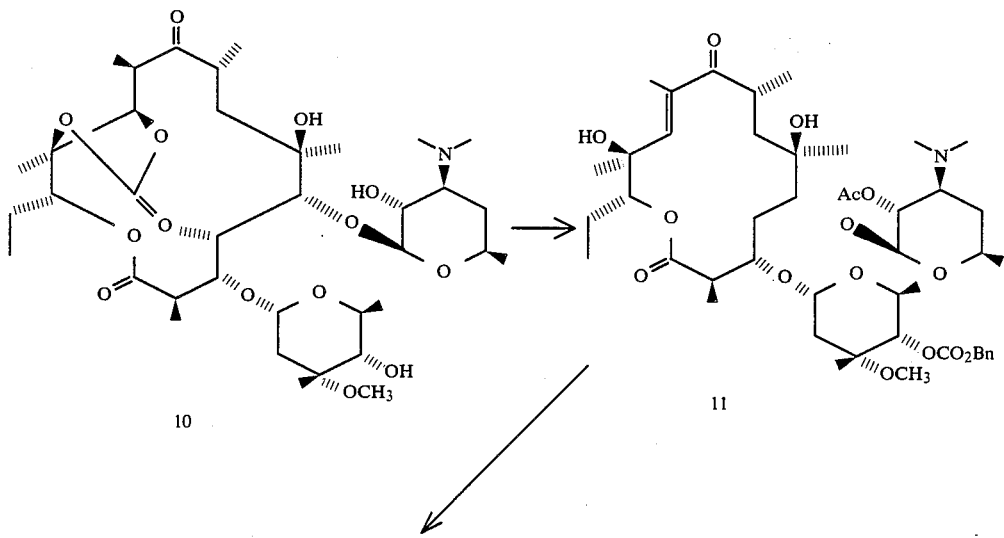

-continued
Scheme 3

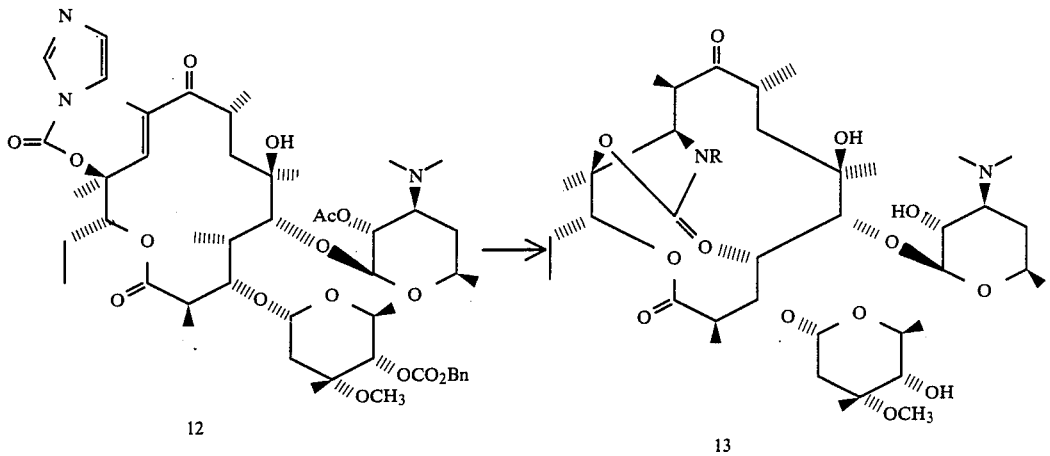

The following examples illustrate the synthesis and use of the compounds and compositions of this invention, without intending to be limitative thereof.

EXAMPLE 1

11-deoxy-6-O-methylerythromycin A-11,12-(N-methoxyethoxypropyl)cyclic carbamate

This compound was prepared by the following method:

B 100.4 g of 6-O-methyl erythromycin A was added to 500 mL methylene chloride and 16.29 g TEA. This mixture was cooled to 4° C. and acetic anhydride was added dropwise. The cooling bath was removed and the mixture was allowed to sit until TLC indicated that the reaction was complete. The reaction was then quenched with 0.5M $NaH_2PO_4$, and the aqueous phase was extracted three times with chloroform. The combined chloroform extracts were dried over $MgSO_4$, and concentrated to dryness to yield 94.8 g of the acetylated product. The crude product was recrystallized from acetonitrile and dried in a vacuum oven at 50° C., affording 80.94 of the 2'acetyl compound (73% yield).

80.13 g of the foregoing product were combined with 600 mL methylene chloride and 49.55 g DMAP. The resulting solution was cooled to −40° C. and 51 mL of benzyl chloroformate were added dropwise with stirring. After 1 hour the mixture was warmed to −20° C. After 24 hours TLC indicated that the reaction was incomplete, and 10 g additional DMAP were added, the mixture was cooled to −35° C., and 10 mL additional benzyl chloroformate were added dropwise. The mixture was then allowed to warm to −20° C. After storage at −20° C. for 2 days, the reaction was quenched with 300 mL 50% sodium bicarbonate solution. The mixture was stirred for 1 hour, the layers were separated, and the organic phase was washed with water and brine, and dried over $MgSO_4$. The solution was concentrated to dryness and the crude solid was recrystallized from acetonitrile and dried in a vacuum oven at 50° C. for about 3 days, to yield 81.72 g of the 2'-acetyl-4"-CBZ compound as a white solid.

10.375 g of the foregoing compound was dissolved in 200 mL dry THF and the solution was cooled to −20° C. 14.6 mL $NaN(TMS)_2$ was added and the solution was stirred for ½ hour. 7.27 g CDI dissolved in 200 mL THF was added dropwise and the reaction mixture was allowed to warm to RT and stored overnight. The reaction was quenched with 150 mL $NaHPO_4$ and extracted with 500 mL ethyl acetate. The organic layer was washed twice with 400 mL aliquots of brine, dried over $MgSO_4$ and concentrated to dryness to provide about 12 g of crude product. The crude solid was column chromatographed on silica gel using 10% methanol in ethyl acetate. Fractions 105 to 150 yielded 4.43 g of the desired acyl imidazole, while fractions 80-101 yielded the cyclic carbonate.

0.99 g of the foregoing acyl imidazole and 3.0 mL 3-(2-methoxy)ethoxypropylamine were stirred at RT for 3 hours. The reaction was quenched by addition of 0.5M $NaHPO_4$ solution and the product was isolated by extraction with chloroform. The crude product was purified by recrystallization from neat ethyl acetate at −10° C. to give 310 mg of white solid. A second crop of 120 mg was collected, and the mother liquor was purified by column chromatography using 3% methanol in chloroform to afford a final 300 mg of product, for a total yield of 730 mg (73%). M.P. 188°–190° C.

720 mg of the foregoing macrolide was suspended in 20 mL methanol and stirred for 4 days. The methanol was then evaporated and the crude product was reduced with hydrogen over Pd/C to cleave the 4"-CBZ group (700 mg 20% Pd/C in 100 mL MeOH at 4 atm. $H_2$ for 2 hours). The solvent was filtered and evaporated to give 532 mg of crude 6-O-methylerythromycin A-11,12-(N-methoxyethoxypropyl)cyclic carbamate as a white solid. This material was purified by flash chromatography using 9:1:0.1 chloroform:methanol:ammonium hydroxide as the elutant. The desired compound was eluted in fractions 15–24. M.P. 189°–191° C.

EXAMPLES 2–22

The following compounds were prepared by the general procedure of Example 1, using the appropriate amine:

2. 11-deoxy-6-O-methyl erythromycin A 11,12 cyclic carbamate
3. 11-deoxy-6-O-methyl erythromycin A 11,12-(N-benzyl)cyclic carbamate
4. 11-deoxy-6-O-methyl erythromycin A 11,12-(N-methyl)cyclic carbamate
5. 11-deoxy-6-O-methyl erythromycin A 11,12-(N-cyclopropyl)cyclic carbamate 6. 11-deoxy-6-O-methyl erythromycin A 11,12-(N-isopropyl)cyclic carbamate
7. 11-deoxy-6-O-methyl erythromycin A 11,12-(N-propyl)cyclic carbamate
8. 11-deoxy-6-O-methyl erythromycin A 11,12-[N-(4-methyl)butyl]cyclic carbamate
9. 11-deoxy-6-O-methyl erythromycin A 11,12-[N-(2-dimethylamino)ethyl]cyclic carbamate
10. 11-deoxy-6-O-methyl erythromycin A 11,12-(N-aminoethyl)cyclic carbamate
11. 11-deoxy-6-O-methyl erythromycin A 11,12-[N-3-(3-aminopropyl)aminopropyl]cyclic carbamate
12. 11-deoxy-6-O-methyl erythromycin A 11,12-[N-(3-dimethylamino)propyl]cyclic carbamate
13. 11-deoxy-6-O-methyl erythromycin A 11,12-[N-2-(4-methylpiperazinyl)ethyl]cyclic carbamate
14. 11-deoxy-6-O-methyl erythromycin A 11,12-[N-alpha-aminopentanoyl]cyclic carbamate
15. 11-deoxy-6-O-methyl erythromycin A 11,12-(N-3-hydroxypropyl)cyclic carbamate
16. 11-deoxy-6-O-methyl erythromycin A 11,12-(N-3-hydroxyethyl)cyclic carbamate
17. 11-deoxy-6-O-methyl erythromycin A 11,12-(N-2-(2-hydroxy)ethoxyethyl)cyclic carbamate The following compounds were prepared from the corresponding 11,12-cyclic carbonate:
18. 11-deoxyerythromycin A 11,12-cyclic carbamate
19. 11-deoxyerythromycin A 11,12-(N-methyl)cyclic carbamate
20. 11-deoxyerythromycin A 11,12-(N-3-hydroxypropyl)cyclic carbamate
22. 11-deoxyerythromycin A 11,12-[N-(3-dimethylamino)ethyl]cyclic carbamate The structure of each was confirmed by $^1$H-NMR, $^{13}$CNMR, elemental analysis and/or high resolution mass spectra.

EXAMPLE 23

The antimicrobial spectra of the compounds of Examples 1–7 were tested by the following method:

Twelve petri dishes containing successive aqueous dilutions of the test compound mixed with 10 ml of sterilized Brain Heart Infusion agar (Difco 0418-01-5) are prepared. Each plate is inoculated with 1:100 (or 1:10 for slow-growing strains, primarily Micrococcus and Streptococcus) dilutions of up to 32 different microorganisms, using a Steers replicator block. The inoculated plates are incubated at 35°–37° C. for 20–24 hours. In addition, a control plate, using BHI agar containing no test compound, is prepared and incubated at the beginning and end of each test.

An additional plate containing a compound having known susceptibility patterns for the organisms being tested and belonging to the same antibiotic class as the test compound is also prepared and incubated as a further control, as well as to provide test-to-test comparability. Erythromycin A was used for this purpose.

After incubation, each disk is read. The MIC is defined as the lowest concentration of drug yielding no growth, a slight haze, or sparsely isolated colonies on the inoculum spot as compared to the growth control.

The results are indicated in the following tables.

TABLE 1

| Organism | MIC (ug/ml) | MIC-Std. |
|---|---|---|
| Compound of Example 1 | | |
| Staph. aureus ATCC 6538P | .06 | .12 |
| Staph. aureus CMX 686B | .12 | .12 |
| Staph. epidermidis 3519 | .06 | .12 |
| Strep. faecium ATCC 8043 | .06 | .06 |
| Strep. pyogenes EES61 | .06 | .06 |
| Strep. pyogenes 930 | 64 | 128 |
| E. coli JUHL | 16 | 16 |
| Compound of Example 2 | | |
| Staph. aureus ATCC 6538P | .1 | .2 |
| Staph. aureus CMX 686B | .1 | .2 |
| Staph. aureus A5177 | .39 | 1.56 |
| Staph. aureus 45 | .1 | .39 |
| Staph. aureus 45 RAR 2 | .2 | .39 |
| Staph. epidermidis 3519 | .05 | .2 |
| Staph. epidermidis 3519 RARI | .05 | .2 |
| Micrococcus luteus 9341 | .05 | .05 |
| Micrococcus luteus 4698 | .39 | — |
| Lactobacillus Casei ATCC 7469 | .05 | .05 |
| Strep. faecium ATCC 8043 | .05 | .1 |
| Strep. bovis A5169 | .02 | .1 |
| Strep. agalactiae CMX 508 | .01 | .05 |
| Strep. pyogenes EES61 | .05 | .02 |
| Strep. pyogenes 930 | >100 | >200 |
| E. coli JUHL | 50 | 50 |
| E. coli SS | .39 | .39 |
| E. coli DC-2 | 50 | 100 |
| E. coli H560 | 3.1 | 25 |
| E. coli KNK 437 | 25 | 100 |
| Ent. aerogenes ATCC 10348 | 100 | 100 |
| Klebsiella pneumoniae 8045 | 50 | 50 |
| Providencia stuartii CMX 640 | >100 | >200 |
| Pseudomonas aeruginosa BMH10 | 50 | 100 |
| Pseudomonas aeruginosa 5007 | 100 | 200 |
| Pseudomonas aeruginosa K799/WT | 50 | 200 |
| Pseudomonas aeruginosa K799/61 | 1.56 | 12.5 |
| Pseudomonas cepacia 2961 | 25 | 200 |
| Acinetobacter SP CMX 669 | 6.2 | 12.5 |
| Staph. aureus ATCC 25923 | .015 | .06 |
| Staph. aureus CMX 739A | .015 | .06 |
| Staph. aureus CMX 730A | .015 | .06 |
| Staph. aureus CMX 705 | .015 | .06 |
| Staph. aureus A-5278 | >128 | >128 |
| Staph. aureus 642A | .03 | .12 |
| Staph. aureus NCTC 10649 | .06 | .06 |
| Staph. aureus GYR 1150 | .03 | .06 |
| Staph. aureus GYR 1162 | .03 | .06 |
| Staph. epidermidis CMX 728 | .03 | .06 |
| Staph. epidermidis CMX 729h | >128 | >128 |
| Staph. epidermidis CMX 724G | >128 | >128 |
| Staph. epidermidis GYR 1151 | .03 | .12 |
| Staph. saprophyticus ATCC 15305 | .03 | .03 |
| Strep. faecalis CMX 736F | .06 | .5 |
| Strep. faecalis CMX 729G | .12 | .5 |
| Strep. faecalis A-5168 | >128 | >128 |
| Strep. faecalis GYR 1164 | .12 | .5 |
| Strep. faecalis GYR 1166 | .06 | .5 |
| Strep. faecalis GYR 1167 | .12 | 4 |
| Strep. faecalis CMX 663F | .5 | 2 |
| Strep. agalactiae CMX 633 | .015 | .015 |
| Strep. pyogenes M79061-139 | .004 | .015 |
| Strep. pyogenes M79061-140 | .004 | .008 |
| Strep. pyogenes M79061-98 | .25 | 1 |
| Strep. pneumoniae CMX 635 | .004 | .015 |
| Strep. pneumoniae CMX 698 | .004 | .008 |
| Strep. pneumoniae 78-008107 | 16 | 32 |
| Strep. pyogenes C203 | .004 | .002 |
| Compound of Example 3 | | |
| Staph. aureus ATCC 6538P | .39 | .2 |
| Staph. aureus CMX 686B | .39 | .2 |
| Staph. aureus A5177 | .78 | .78 |
| Staph. aureus 45 | .1 | .1 |
| Staph. aureus 45 RAR 2 | .39 | .2 |
| Staph. epidermidis 3519 | .2 | .1 |
| Staph. epidermidis 3519 RARI | .2 | .1 |
| Lactobacillus Casei ATCC 7469 | .05 | .02 |
| Strep. faecium ATCC 8043 | .1 | .05 |
| Strep. bovis A5169 | .02 | .01 |
| Strep. agalactiae CMX 508 | .02 | .05 |
| Strep. pyogenes EES61 | .02 | .02 |
| Strep. pyogenes 930 | 100 | >100 |

TABLE 1-continued

| Organism | MIC (ug/ml) | MIC-Std. |
|---|---|---|
| Micrococcus luteus 9341 | .05 | .02 |
| E. coli Juhl | 25 | 50 |
| E. coli SS | .39 | .2 |
| E. coli DC-2 | 25 | 50 |
| E. coli H560 | 6.2 | 12.5 |
| E. coli KNK 437 | 25 | 50 |
| Ent. aerogenes ATCC 13048 | 50 | 50 |
| Klebsiella pneumoniae 8045 | 25 | 50 |
| Pseudomonas aeruginosa BMH10 | 25 | 100 |
| Pseudomonas aeruginosa 5007 | >100 | >100 |
| Pseudomonas aeruginosa K799/WT | >100 | >100 |
| Pseudomonas aeruginosa K799/61 | 3.1 | 1.56 |
| Acinetobacter SP CMX 669 | 50 | 6.2 |
| Pseudomonas cepacia 2961 | 50 | >100 |
| Providencia stuartii CMX 640 | >100 | >100 |
| Compound of Example 4 | | |
| Staph. aureus ATCC 6538P | .1 | .2 |
| Staph. aureus CMX 686B | .1 | .2 |
| Staph. aureus A5177 | .39 | 1.56 |
| Staph. aureus 45 | .1 | .2 |
| Staph. aureus 45 RAR 2 | .2 | .39 |
| Staph. epidermidis 3519 | .2 | .210 tap |
| h. epidermidis 3519 RARI | .2 | .2 |
| Lactobacillus Casei ATCC 7469 | .01 | .02 |
| Strep. faecium ATCC 8043 | .05 | .05 |
| Strep. bovis A5169 | .02 | .02 |
| Strep. agalactiae CMX 508 | .02 | .02 |
| Strep. pyogenes EES61 | .01 | .02 |
| Strep. pyogenes 930 | >100 | >100 |
| Micrococcus luteus 9341 | .01 | .02 |
| E. coli Juhl | 25 | 50 |
| E. coli SS | .1 | .2 |
| E. coli DC-2 | 25 | 50 |
| E. coli H560 | 12.5 | 25 |
| E. coli KNK 437 | 50 | 100 |
| Ent. aerogenes ATCC 10348 | 50 | 50 |
| Klebsiella pneumoniae 8045 | 50 | 50 |
| Pseudomonas aeruginosa BMH10 | 50 | 100 |
| Pseudomonas aeruginosa 5007 | 100 | >100 |
| Pseudomonas aeruginosa K799/WT | 100 | 100 |
| Pseudomonas aeruginosa K799/61 | .78 | 1.56 |
| Acinetobacter SP CMX 669 | 12.5 | 6.2 |
| Pseudomonas cepacia 2961 | 100 | >100 |
| Providencia stuartii CMX 640 | >100 | >100 |
| Micrococcus luteus 4698 | .05 | .1 |
| Compound of Example 5 | | |
| Staph. aureus ATCC 6538P | .39 | .2 |
| Staph. aureus CMX 686B | .39 | .2 |
| Staph. aureus A5177 | 1.56 | 1.56 |
| Staph. aureus 45 | .2 | .2 |
| Staph. aureus 45 RAR 2 | .39 | .39 |
| Staph. epidermidis 3519 | .39 | .2 |
| Staph. epidermidis 3519 RARI | .39 | .2 |
| Lactobacillus Casei ATCC 7469 | .05 | .02 |
| Strep. faecium ATCC 8043 | .1 | .05 |
| Strep. bovis A5169 | .02 | .02 |
| Strep. agalactiae CMX 508 | .02 | .02 |
| Strep. pyogenes EES61 | .02 | .02 |
| Strep. pyogenes 930 | >100 | >100 |
| Micrococcus luteus 9341 | .05 | .02 |
| E. coli Juhl | 50 | 50 |
| E. coli SS | .2 | .2 |
| E. coli DC-2 | 100 | 50 |
| E. coli H560 | 25 | 25 |
| E. coli KNK 437 | 100 | 100 |
| Ent. aerogenes ATCC 13048 | 100 | 50 |
| Klebsiella pneumoniae 8045 | 100 | 50 |
| Pseudomonas aeruginosa BMH10 | 100 | 100 |
| Pseudomonas aeruginosa 5007 | >100 | >100 |
| Pseudomonas aeruginosa K799/WT | >100 | 100 |
| Pseudomonas aeruginosa K799/61 | 6.2 | 1.56 |
| Acinetobacter SP CMX 669 | 25 | 6.2 |
| Pseudomonas cepacia 2961 | >100 | >100 |
| Providencia stuartii CMX 640 | >100 | >100 |
| Micrococcus luteus 4698 | .2 | .1 |

EXAMPLE 24

In the manner of Example 23, the efficacy of compounds of this invention were tested against numerous strains of *Haemophilus influenzae*. Results were as follows:

TABLE 2

| | MIC (ug/ml) | | | |
| | Compound of Example: | | | |
| Strain: | 12 | 9 | 15 | 16 |
|---|---|---|---|---|
| 5036B | 1 | .5 | 1 | 1 |
| 504 | 1 | 1 | 1 | 1 |
| 519A | .5 | .5 | .5 | .5 |
| 566A | 1 | .5 | 1 | 1 |
| 588A | .5 | .25 | 1 | .5 |
| 632A | .5 | .5 | 1 | 1 |
| 667A | .5 | .25 | 1 | 1 |
| 747C | .5 | .25 | .5 | .5 |
| 751 | .5 | .25 | 1 | 1 |
| DILL AMP R | .5 | .25 | .5 | .5 |
| SPK AMP R | .5 | .25 | 1 | 1 |
| SOL AMP R | .5 | .25 | .5 | .5 |
| 1177 | .5 | .5 | 1 | 1 |
| 1435 | .25 | .12 | .5 | .25 |
| ATCC 9006 | .5 | .25 | .5 | .5 |
| ATCC 9795 | .5 | .25 | .5 | .5 |
| ATCC 19418 | 1 | .5 | 1 | .5 |
| ATCC 10211 | 1 | .5 | 1 | 1 |

Although the MIC of Erythromycin A was not simultaneously measured in this test, Erythromycin A typically exhibits a MIC of from 1 to 4 micrograms per mL against these organisms.

EXAMPLE 25

The in vitro hepatotoxicity of compounds of this invention were determined. Compounds were incubated with hepatic parenchymal cells and both the medium filtrate and the cell supernatant were analyzed for lactate dehydrogenase activity using standard methods. LDH activity has been shown to correlate with cell membrane disruption and is regarded as a reliable indicator of cell injury. The ratio of medium filtrate LDH activity to media plus cellular LDH activity is calculated as a percentage value. This index was used to evaluate the degree of drug toxicity. The LDH indices for the compounds of this invention were significantly lower than those of the corresponding 11,12-cyclic carbonates, and at least one was better than erythromycin A, which is generally considered the least toxic active erythromycin compound.

EXAMPLE 26

Compounds of this invention have been tested for gastrointestinal stimulating activity in a dog model at 4 mg/kg intravenously. Contractions in the gut were recorded with surgically implanted strain gauges. The contractile scores were determined according to the method of Jacoby, et al., as described in the article "Gastrointestinal Actions of Metoclopramide," *Gastroenterology*, Vol. 52, No. 4 (1967), pp. 676-684 by giving a numerical score to the height of each recorded contraction in the one hour period after administration of the test compound. A gastrointestinal motility index was expressed as the ratio of the contractility score for the test compound to the score for erythromycin A lactobinate. Ratios were calculated for the stomach, duodenum and jejunum, and a final arithmetic mean index was calculated and reported in Table 1.

TABLE 3

| Substituent: | Gastrointestinal Motility Index | |
|---|---|---|
| | Ery A | 6-O—Me—Ery A |
| None | 1.00 | — |
| 11,12-N—methyl cyclic carbamate | 5.83 | 1.27 |
| 11,12-cyclic carbamate | 3.60 | 1.18 |
| 11,12-N—dimethylaminoethyl cyclic carbamate | — | .013 |

Administration of erythromycin A and 6-O-methyl erythromcyin A lactobionates at 4 mg/kg intravenously resulted in pronounced stimulation of the stomach, duodenum, jejunum and ileum. Administration of the 11,12-N-dimethylaminoethyl carbamate of the latter compound at 4 mg/kg intravenously resulted in negligible apparent stimulation of the gastrointestinal tissues. This illustrates that some compounds of this invention are devoid of or have significantly less gastrointestinal stimulation than the parent compounds at this dosage level.

EXAMPLE 27

Acute Mouse Protection Activity of 11-deoxy-6-O-methyl erythromycin A 11,12-Cyclic carbamate The acute mouse protection test is conducted on ten mice with each of three levels of of drug. Mouse mortality is used to calculate an $ED_{50}$ value, i.e., the dose of drug required to protect 50% of the test animals against death due to the inoculum challenge.

The acute mouse protection test is conducted on female, Swiss albino mice, 18–20 grams in weight. The mice are injected intraperitoneally with an 18-hour culture of the indicated test organism diluted sufficiently to provide the desired $LD_{50}$ value. To check the potency of the inoculum, a titration of the indicated test organism is carried out in control animals. The treatment group of animals is dosed with the test compound at 1 and 5 hours post-infection and observed for 7 days. The $ED_{50}$ values are calculated using the mortality data collected. Results are indicated in the following table.

TABLE 4

Organism: *Staph. aureus* NCTC 10649
Culture Medium: BHI
Dosage medium: PBS
Dosage Route: Oral

| | Test Compound | Ery A |
|---|---|---|
| Dosage (mg/kg)/# Died: | 9.4/10 | 15.6/10 |
| | 62.5/7 | 37.5/4 |
| | 150.0/0 | 250.0/0 |
| $ED_{50}$ (mg/kg/day): | 34.4 | 75.7 |
| Upper conf. limit: | 46.4 | 109.6 |
| Lower conf. limit: | 25.5 | 52.2 |

Organism: *Staph. aureus* NCTC 10649
Culture Medium: BHI
Dosage medium: Carboxymethylcellulose
Dosage Route: Oral

| | Test Compound | Ery A |
|---|---|---|
| Dosage (mg/kg)/# Died: | 9.4/10 | 15.6/8 |
| | 62.5/7 | 37.5/5 |
| | 150.0/0 | 250.0/0 |
| $ED_{50}$ (mg/kg/day): | 45.2 | 48.8 |
| Upper conf. limit: | 65.4 | 91.9 |
| Lower conf. limit: | 31.3 | 26.0 |

Organism: *Staph. aureus* NCTC 10649
Culture Medium: BHI
Dosage medium: Injectable solution
Dosage Route: Subcutaneous

| | Test Compound | Ery A |
|---|---|---|
| Dosage (mg/kg)/# Died: | 2.5/9 | 2.5/10 |
| | 10.0/1 | 10.0/6 |
| | 40.0/0 | 40.0/0 |
| $ED_{50}$ (mg/kg/day): | 5.0 | 10.9 |
| Upper conf. limit: | 7.9 | 14.7 |
| Lower conf. limit: | 3.2 | 8.1 |

What is claimed is:

1. A compound of the formula

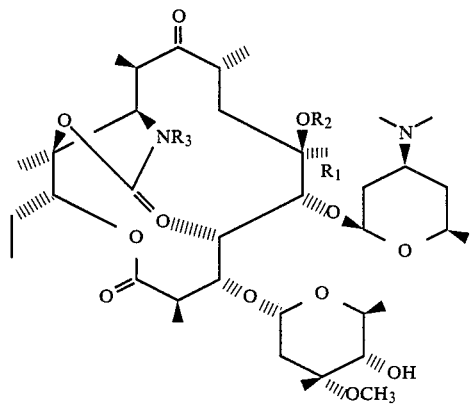

where $R_1$ is selected from hydroxyl or O-acyl of 2 to 20 carbon atoms, $R_2$ is hydrogen or methyl and $R_3$ is hydrogen, alkyl, alkoxy, dimethylaminoalkyl, or haloalkyl, and pharmaceutically acceptable salts thereof.

2. A compound according to claim 1 wherein $R_2$ is methyl.

3. A compound according to claim 2 wherein $R_1$ is hydroxyl and $R_3$ is 2-dimethylaminoethyl.

4. An antibacterial composition in unit dosage form, comprising an antibacterially effective amount of a compound according to claim 1 in combination with a pharmaceutical carrier.

5. A method of treating and preventing bacterial infections in humans and lower animals in need of such treatment, comprising administering to the human or lower animal a therapeutically effective amount of the composition of claim 4.

* * * * *